United States Patent [19]
Agarwala

[11] Patent Number: 5,961,542
[45] Date of Patent: Oct. 5, 1999

[54] MEDICAL STIMULATOR WITH INTENSITY CONTROL AND MODE OF OPERATION OVERRIDE

[75] Inventor: Poonam Agarwala, New Brighton, Minn.

[73] Assignee: Empi Corp., St. Paul, Minn.

[21] Appl. No.: 09/021,795

[22] Filed: Feb. 11, 1998

[51] Int. Cl.⁶ ...................................................... A61N 1/36
[52] U.S. Cl. ............................................................ 607/63
[58] Field of Search ................................. 607/46, 59, 62, 607/63, 72

[56] References Cited

U.S. PATENT DOCUMENTS

| | | |
|---|---|---|
| 4,177,819 | 12/1979 | Kofsky et al. ............................. 607/62 |
| 4,582,063 | 4/1986 | Mickiewicz et al. ...................... 607/63 |
| 5,048,523 | 9/1991 | Yamasawa et al. ........................ 607/72 |
| 5,653,739 | 8/1997 | Maurer et al. ............................. 607/46 |

*Primary Examiner*—William E. Kamm
*Attorney, Agent, or Firm*—Kinney & Lange, P.A.

[57] ABSTRACT

A medical stimulator provides periodic treatment modes featuring an on time in which a pulse train of stimulation signals are delivered to the patient, and an off time in which no stimulation signals are provided. The rate and/or intensity of the pulse train may be modulated during the on time cycles. An intensity control is provided to allow the patient to increase or decrease intensity at any time. When the intensity control is actuated by the patient, the pulse train is automatically switched to a continuous mode in which a continuous train of pulses is provided while intensity is adjusted.

6 Claims, 7 Drawing Sheets

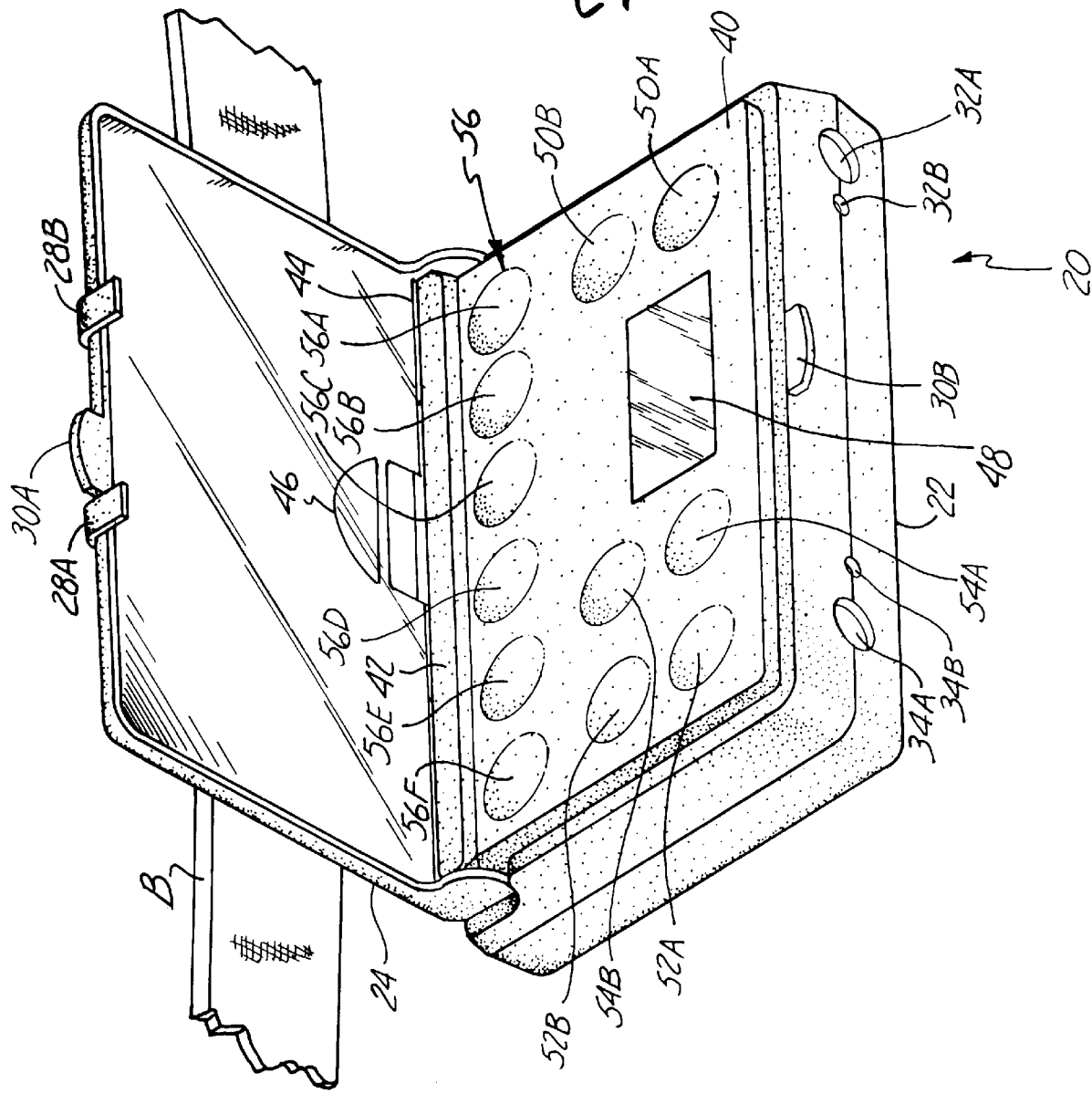

MEDICAL STIMULATOR WITH INTENSITY CONTROL AND MODE OF OPERATION OVERRIDE

BACKGROUND OF THE INVENTION

The present invention relates to a medical stimulator which provides an electrical stimulation signal, in the form of a continuous or interrupted train of pulses to a patient. More particularly, the present invention relates to a medical stimulator with an intensity control which allows the patient to vary the intensity of the stimulation signals produced by the stimulator.

Medical stimulators which provide electrical stimulation signals to a patient are used to provide short and long term pain relief though transcutaneous electrical nerve stimulation (TENS) and to stimulate and rehabilitate muscles through neuromuscular stimulation (NMS). These types of medical stimulators typically use electrodes which are attached to the patient's skin. The TENS or NMS stimulator sends electrical stimulation signals into the muscles and nerves through the attached electrodes. The electrical stimulation signals produced by a TENS or NMS stimulator are in the form of a train of electrical pulses which may be modulated in rate and/or intensity. Medical stimulators commonly use periodic treatment modes for various reasons, such as to reduce accommodation and to reduce fatigue which can be produced by a continuous train of stimulation pulses. The periodic treatment modes generally have an on time and an off time cycle. A train of pulses forming the stimulation signal is delivered during the on time, and no pulses are delivered during the off time. The length of the on time and the off time may vary from mode to mode, and the rate and intensity of the pulses delivered during on time may also vary from mode to mode.

Many medical stimulators also provide a continuous mode in which a continuous train of pulses is provided as an output. The continuous mode is usually provided for initially setting the intensity of the stimulation. During treatment, the patient can increase or decrease the intensity at any time using an intensity control on the stimulator.

If the intensity is increased while the stimulator is operating in a periodic treatment mode and is in the "off time" of the cycle, or during a reduced stimulation time in a modulation mode, the patient cannot initially feel the increased intensity. When the stimulator switches to the "on time" portion of the cycle, or to the full stimulation time during a modulation mode, the patient can be unpleasantly surprised by the onset of the full intensity stimulation.

In the past, some stimulators have disabled the intensity control while the stimulator is operating in a periodic treatment or modulation mode. This can be frustrating to the patient, who wants to adjust the intensity while the stimulator is operating. The alternative has been to allow the patient to change the intensity at any time, with the risk being an unpleasant surprise if the intensity is adjusted during a off time or a reduced stimulation time.

SUMMARY OF THE INVENTION

The present invention is a medical stimulator which allows a patient to vary the intensity setting of stimulation at any time. When the intensity control is actuated by the patient, the stimulator automatically switches to a continuous mode which outputs a continuous train of pulses. This automatic switching occurs regardless of the treatment mode that had been in operation at the time that the patient actuated the intensity control.

When adjustment of the intensity control is ended, the stimulator automatically returns to the treatment mode in which it had been operating before the intensity control was actuated. With the present invention, the patient is assisted in his or her desire to modify intensity, rather than being prevented from changing intensity settings, or being surprised by the onset of full stimulation.

BRIEF DESCRIPTION OF THE DRAWINGS

FIGS. 1A–1C are perspective views of a TENS device in a closed position and in first and second open positions, respectively.

DETAILED DESCRIPTION OF THE PREFERRED EMBODIMENTS

A preferred embodiment of transcutaneous electrical nerve stimulation (TENS) device 20 is shown in FIGS. 1A–1C, 2 and 3. TENS device 20 includes case 22 and back cover 24. Back cover 24 is clipped to a patient's belt B by belt clip 26 when TENS device 20 is in use by the patient.

Figure 1A:
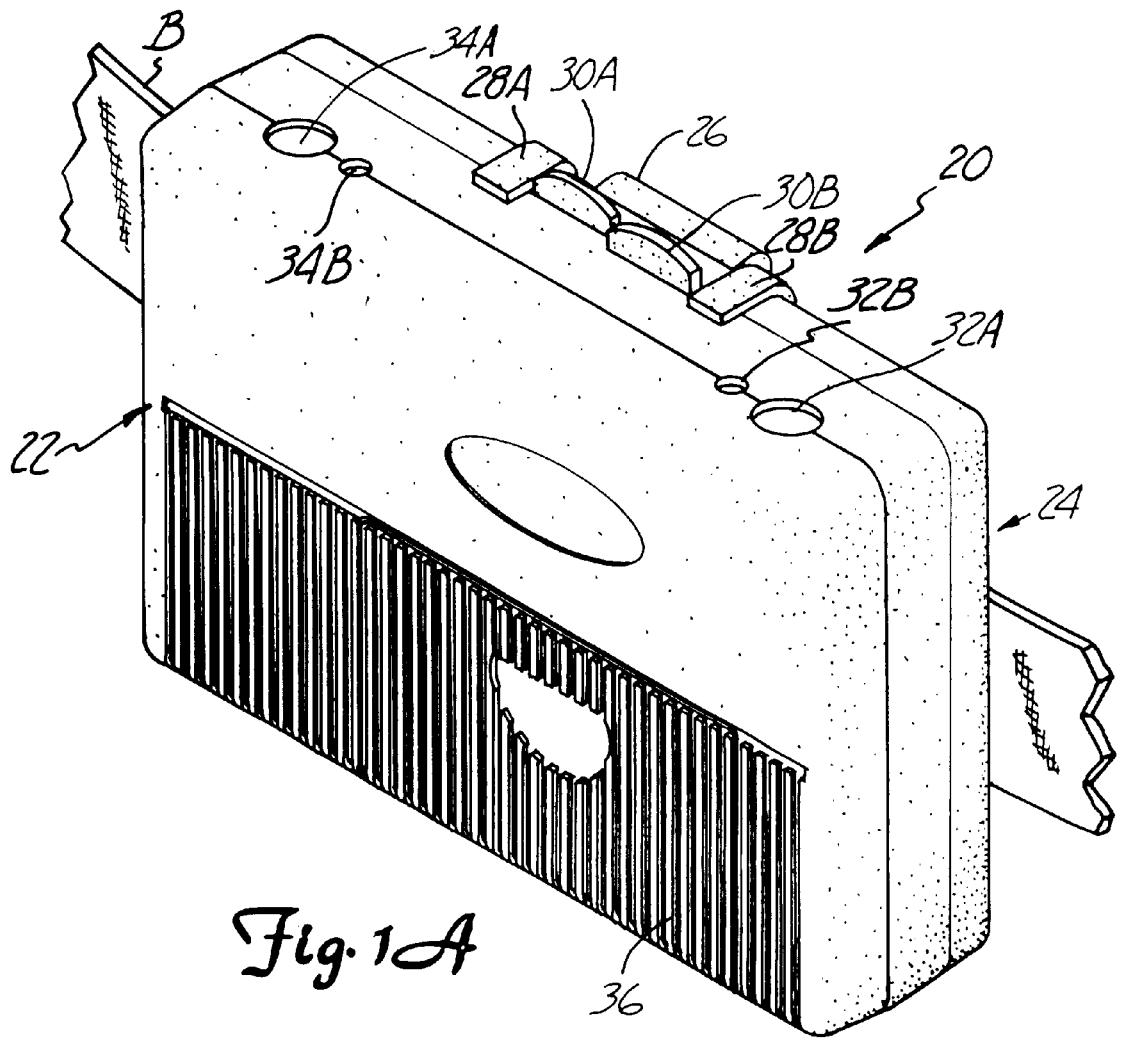

Back cover 24 is pivotally connected to case 22. In FIG. 1A, case 22 and back cover 24 are adjacent one another in a closed position. A pair of resilient clips or fingers 28A and 28B extend from the top of back cover 26 and hold case 22 in the closed position. Tab 30A (at the top of back cover 24) and tab 30B (at the top of case 22) are pried apart to release case 22 from fingers 28A and 28B and open TENS device 20. In the embodiment shown in FIG. 1A, TENS device 20 provides two output channels ("channel 1" and "channel 2"). Output terminals 32A and 32B are the channel 1 output terminals, while terminals 34A and 34B are the channel 2 output terminals.

TENS device 20 is battery powered. Access to the battery compartment is provided through battery compartment cover 36 on the front side of case 22.

In FIG. 1B, case 22 has been pivoted to a first open position, where control panel 40 is accessible for viewing and actuation by the patient. In FIG. 1B, case 22 is oriented at approximately 90° to back cover 24 so that case 22 is generally horizontal. Control panel 40 is oriented so that it can be read and used by the patient when device 20 is mounted on belt B (or a waistband or pocket) and is open as shown in FIG. 1B.

Figure 1C:
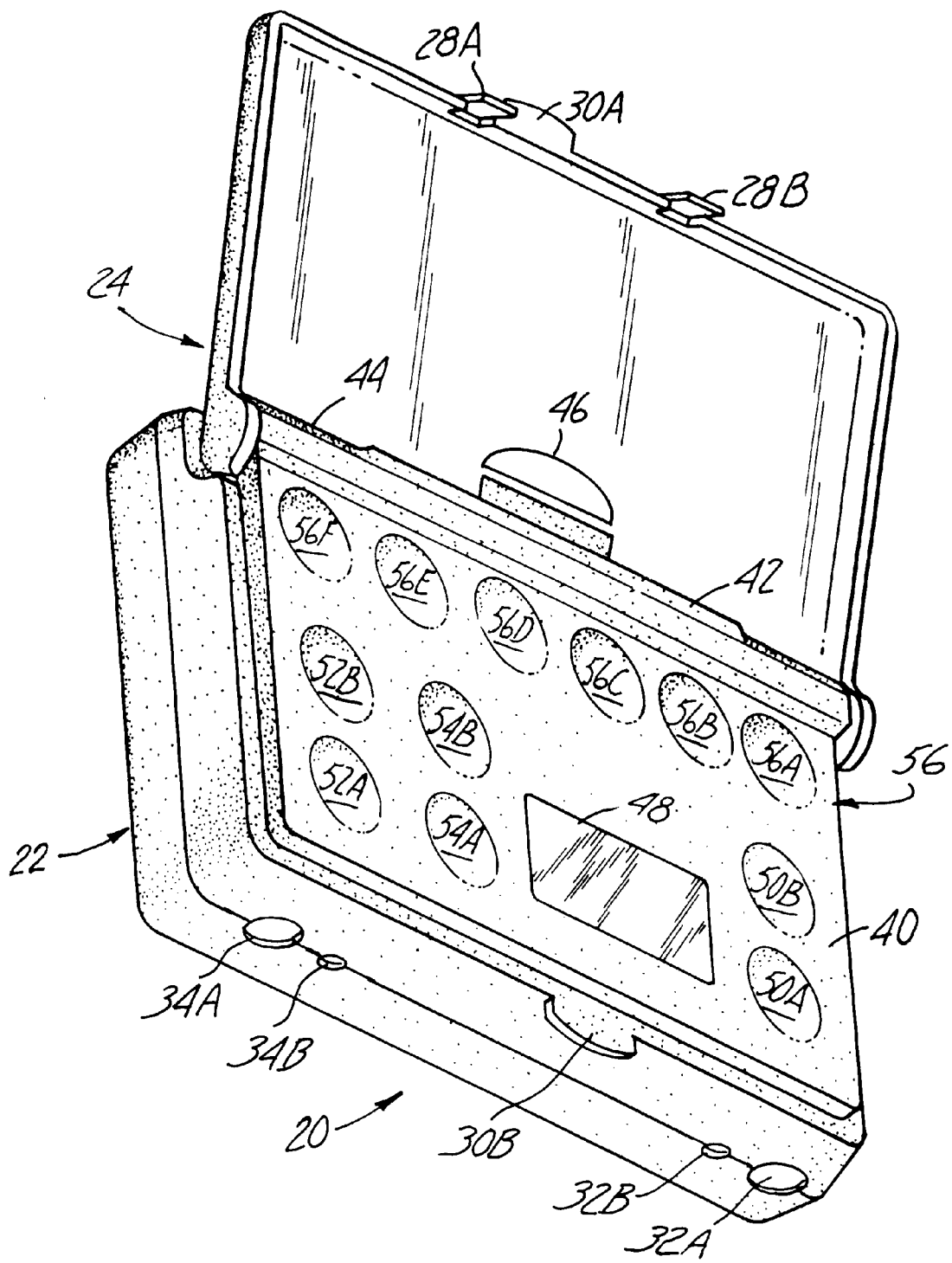
Figure 2:
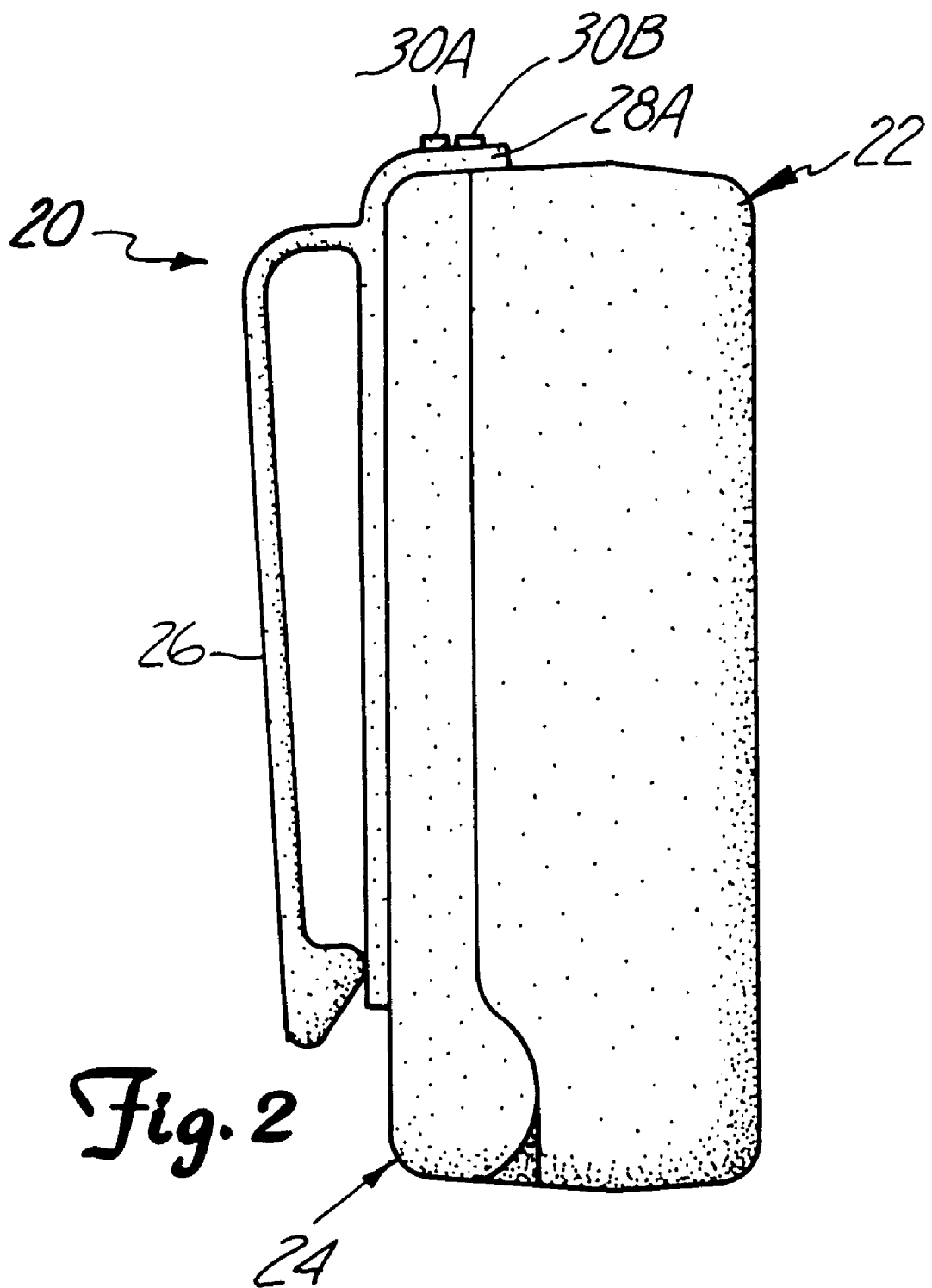
FIG. 2 is a side view of the TENS device.

FIG. 1C shows case 22 as it has been pivoted beyond the first open position to a second open position. In this second open position, case 22 and cover 24 are at an angle of approximately 180° to one another. The second open position is particularly useful when TENS device 20 is placed on a flat surface, such as a table.

The first open position (shown in FIG. 1B) is defined by shoulder 42 (FIGS. 1C and 3) on case 22. When tabs 30A and 30B are pried apart to release case 22 from fingers 28A and 28B, case 22 pivots outward and downward until lower edge 44 of back cover 24 engages shoulder 42.

Back cover 24 is molded plastic, and has sufficient resiliency so that it can be flexed. By gently pressing on shoulder release region 46 of back cover 24, the patient (or clinician) can flex the center portion of back cover 24 sufficiently to move lower edge 44 out of engagement with shoulder 42. This allows case 22 to continue to pivot downward with respect to back cover 24.

Figure 3:
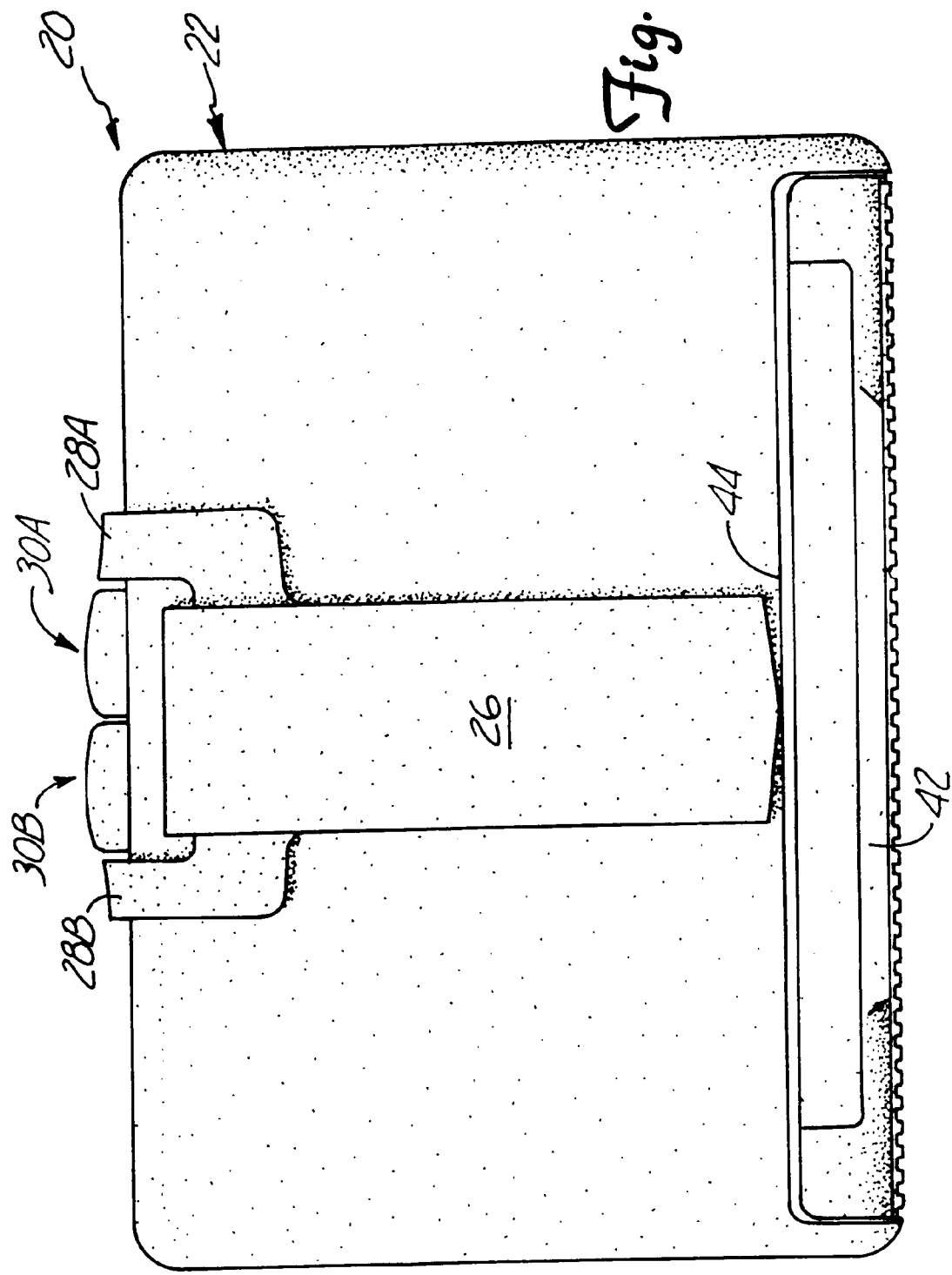
FIG. 3 is a rear view of the TENS device.

As shown in FIG. 1C and FIG. 3, shoulder 42 does not extend the entire width of case 22, but rather is located in a central part. This allows clearance to be achieved between shoulder 42 and the center portion of lower edge 44 of back cover 24 when pivoting case 22 to the second open position illustrated in FIG. 1C.

Figure 4:
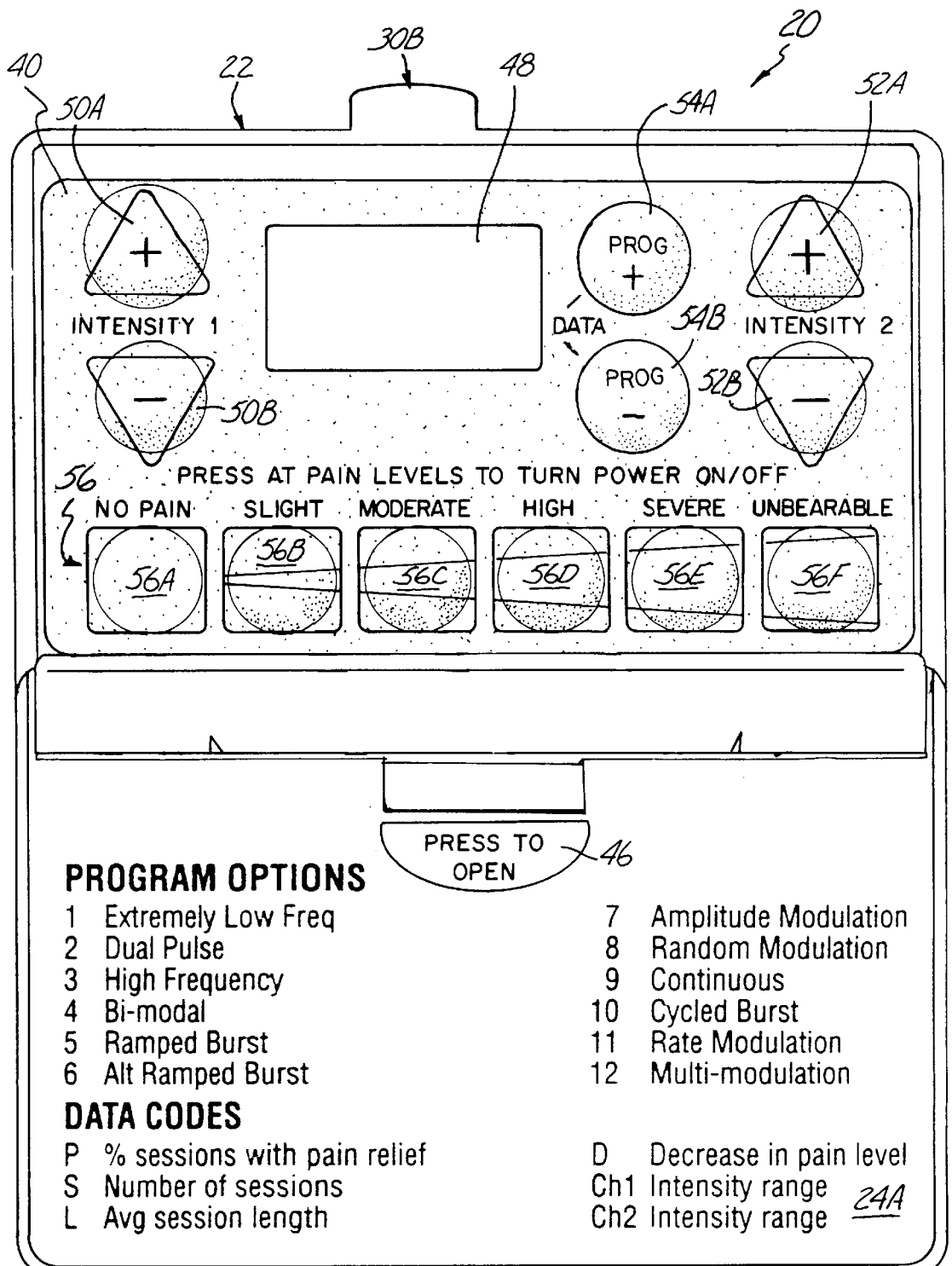
FIG. 4 is a front view of the control panel and the inside surface of the cover with the TENS device in the second open position.

As shown in generally FIGS. 1B and 1C, and in more detail in FIG. 4, control panel 40 includes display 48, channel 1 intensity control inputs 50A and 50B, channel 2 intensity control inputs 52A and 52B, pre-programmed (PROG) selection inputs 54A and 54B, and electronic pain intensity scale 56 (with inputs 56A–56F).

Display 48 allows the patient to view inputted data, current intensity settings, and treatment results. Display 48 also allows the clinician to retrieve data concerning the effectiveness of a patient's treatment.

The channel 1 intensity control inputs 50A and 50B and channel 2 intensity control inputs 52A and 52B allow the patient to regulate the intensity of the treatment being administered. In the preferred embodiment, the channel 1 intensity control inputs 50A and 50B and channel 2 intensity control inputs 52A and 52B are labeled "Intensity". Inputs 50A and 52A are labeled with a "+" denoting an increase in intensity, while inputs 50B and 52B are labeled with a "–" denoting a decrease in intensity.

The PROG selection inputs 54A and 54B are designed to allow the patient to select from a number of pre-programmed treatment regimens which are listed on inside surface 24A of cover 24 as "Program Options". In the preferred embodiment, the PROG selection inputs 54A and 54B are labeled "PROG+" and "PROG–", respectively. The PROG+ input 54A allows the patient to scroll forward through the list of regimens, and PROG– input 54B allows the patient to scroll backwards through the same list.

By pressing both of the PROG+ and PROG– selection inputs 54A and 54B simultaneously during power up, the clinician is able to access the data menu. The data menu provides the clinician with information related to the patient's treatment such as number of sessions, decrease in pain relief, percent of sessions with pain relief, average session length, channel 1 intensity range, and channel 2 intensity range. The data menu is listed on inside surface 24A of cover 24 as "Data Codes".

By pressing both PROG+ and PROG– selection inputs 54A and 54B during treatment, the clinician is able to change the rate of the selected pre-programmed regimen.

Electronic pain intensity scale 56 is preferably formed by an array of membrane switch inputs 56A–56F. The different areas of scale 56 are labelled to represent the different levels of perceived pain inputted by the patient. Each area is associated with one of the plurality of inputs 56A–56F. Each input 56A–56F represents a different level of perceived pain. In the preferred embodiment, scale 56 ranges from "No Pain" input 56A to "Slight" input 56B, to "Moderate" input 56C, to "High" input 56D, to "Severe" input 56E, to "Unbearable" input 56F. Therefore, the plurality of inputs 56A–56F, from left to right, represent increasing levels of perceived pain. As will later be described, depending upon which of the plurality of indicator inputs is selected, pain data is produced and stored.

Figure 5:
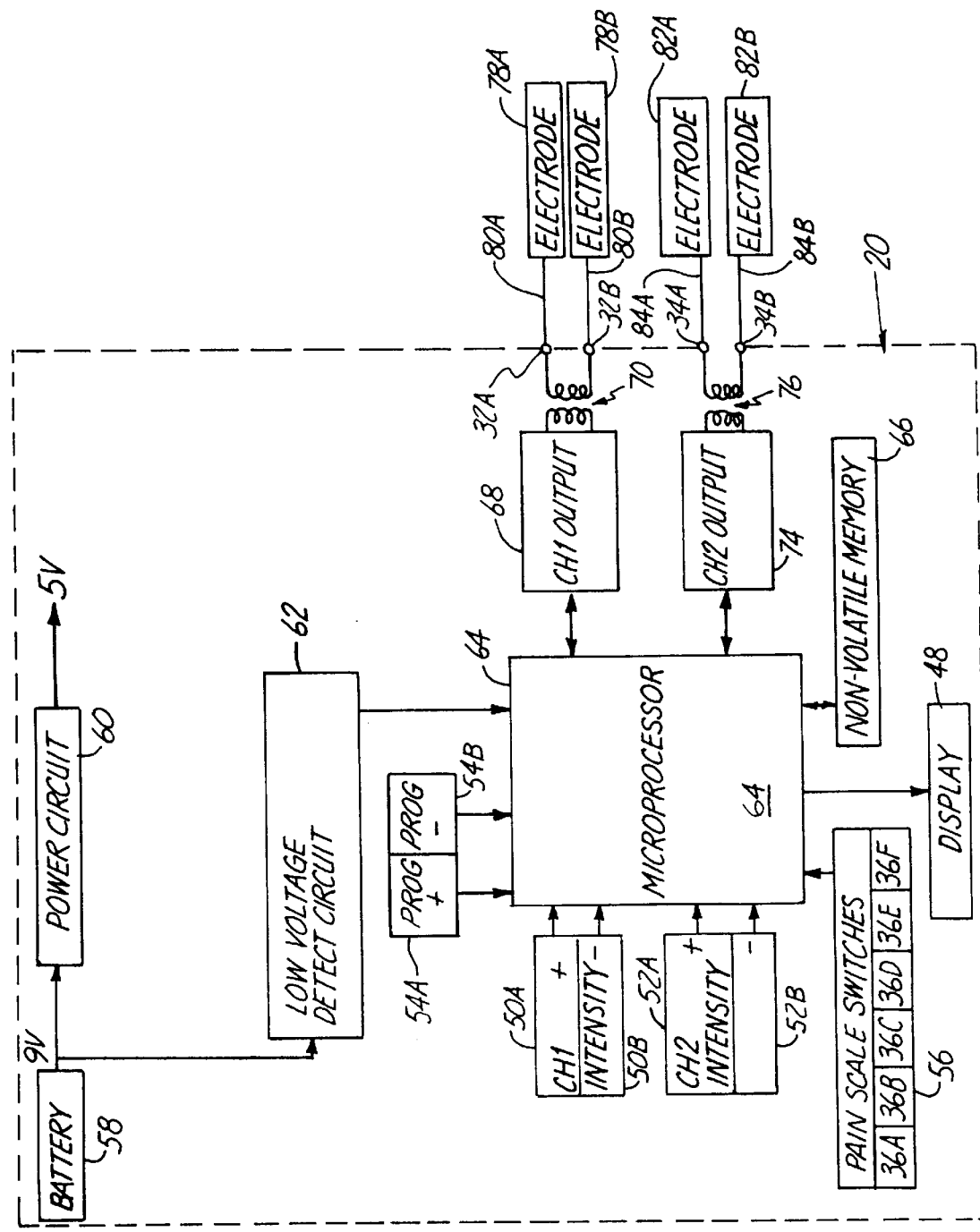
FIG. 5 is an electrical block diagram of the TENS device.

FIG. 5 is a block diagram of TENS device 20, which provides further detail of the inner components. TENS device 20 includes display 48, channel 1 intensity control inputs 50A and 50B, channel 2 intensity control inputs 52A and 52B, PROG selection inputs 54A and 54B, electronic pain intensity scale inputs 56A–56F, battery 58, power circuit 60, low voltage detect circuit 62, microprocessor 64, non-volatile memory 66, channel 1 output driver 68, channel 1 output transformer 70, channel 1 output terminals 32A and 32B, channel 2 output driver 74, channel 2 output transformer 76, and channel 2 output terminals 34A and 34B. TENS electrodes 78A and 78B are connected, through lead wires 80A and 80B, to channel 1 output terminals 32A and 32B, respectively. Similarly, TENS electrodes 82A and 82B are connected, through lead wires 84A and 84B, to channel 2 output terminals 34A and 34B.

Before a treatment session can begin, the patient must indicate his or her present level of perceived pain on the electronic pain intensity scale 56. In the preferred embodiment, the patient has six choices (inputs 56A–56F) to aid in subjectively assessing his or her pain levels. As previously discussed, these choices range from "No Pain" to "Unbearable". The patient enters his or her perceived level of pain by pressing a corresponding input on the electronic pain intensity scale 56. During non-operation, device 20 is normally powered up, but the microcontroller 64 is maintained in a stop mode to minimize power consumption. When any input (56A–56F) on scale 56 is pressed, a signal is sent to microprocessor 64. The signal activates microprocessor 64 and pain level data from the electronic pain intensity scale 56 is read and stored in memory 66 by microprocessor 64. Microprocessor 64 also stores the current time, which is maintained by the real time clock within microprocessor 64. After an initial pain level has been entered, treatment can begin. The patient selects one of the pre-programmed regimens by scrolling through the list of pre-programmed regimens using the PROG selection inputs 54A and 54B and viewing the selection on display 48. The patient uses channel 1 and channel 2 intensity control inputs 50A and 50B and 52A and 52B to adjust stimulation intensity for channels 1 and 2.

Microprocessor 64 controls channel 1 output driver 68 based upon the regimen selected through PROG selection inputs 54A and 54B and the intensity level selected through channel 1 intensity control inputs 50A and 50B. The output of channel 1 output driver 68 is supplied through transformer 70 to channel 1 output terminals 32A and 32B. TENS electrodes 78A and 78B are connected through lead wires 80A and 80B, respectively, to channel 1 output terminals 32A and 32B. TENS electrodes 78A and 78B are applied to the skin of the patient at the desired location to provide pain relief.

Similarly, microprocessor 64 controls channel 2 output driver 74 based upon the regimen selected through PROG selection inputs 54A and 54B and the intensity level selected through channel 2 intensity control inputs 52A and 52B. The output of channel 2 output driver 74 is supplied through transformer 76 to channel 2 output terminals 34A and 34B. TENS electrodes 82A and 82B are connected through lead wires 84A and 84B, respectively, to channel 2 output terminals 34A and 34B. The output of channel 2 output driver 74, therefore, is supplied to the patient through TENS electrodes 82A and 82B.

Tens device 20 is configured to provide a periodic electrical stimulation signal having an on time and a off time cycle. The train of pulses forming the stimulation signal are delivered during the on time, and no pulses are delivered during the off time. During operation, the patient can increase or decrease the intensity level of either channel. When a patient actuates channel 1 intensity control inputs 50A or 50B, or channel 2 intensity control inputs 52A or 52B, microprocessor 64 automatically changes the operating mode for the selected channel to a continuous mode (on time). Therefore, if one of the channel 1 intensity control inputs 50A or 50B is actuated, microprocessor 64 causes the output on channel 1 to switch to a continuous mode in which a continuous train of pulses is supplied from channel 1 output driver 68, through channel 1 output transformer 70 and channel 1 output terminals 32A and 32B to electrodes 78A and 78B.

Similarly, if one of the channel 2 intensity control input 52A or 52B is actuated, microprocessor 64 automatically causes the output of channel 2 output driver 74 to generate a continuous train of pulses through channel 2 output transformer 76 and channel 2 output terminals 34A and 34B to electrodes 82A and 82B.

While the adjustment of intensity on a channel is ongoing, a continuous train of pulses is provided on that channel. This allows the patient to receive the maximum stimulation for the particular intensity setting which is being selected.

Once the patient stops actuating the intensity control inputs 50A, 50B, 52A or 52B, the corresponding output on channel 1 or channel 2 returns to whatever operating mode existed before the intensity level selection process. Microprocessor 64 causes the outputs of the channel 1 output driver 68 and channel 2 output driver 74 to resume based upon the regimen which has been programmed and the intensity level which was selected during the intensity level selection process. The resumption of the treatment mode occurs when microprocessor 64 determines that the intensity controls 50A, 50B, 52A and 52B have been inactive for a predetermined time, such as two seconds.

Microprocessor 64 stores the pain level input from one of pain level switches 56A–56F, together with the starting time when the pain scale switch was actuated, and the intensity setting for channel 1 and channel 2. If, during the course of a treatment session, the patient changes the intensity level, the new level and the time of change is recorded by microprocessor 64 in non-volatile memory 66. To end a treatment session, the patient again presses one of the pain scale switches 56A–56F. The patient has been instructed to press the input 56A–56F representing perceived pain at the time that the treatment is stopped. Upon receiving the second key press from pain scale switches 56A–56F, microprocessor 64 controls output drivers 68 and 74 to stop the treatment. In addition, microprocessor 64 records the final pain scale level (based upon which switch 56A–56F was pressed) together with the time. The recorded time can either be a real clock time, or can simply be a duration since the treatment session started.

TENS device 20 is able to aid the clinician in determining the effectiveness of the pain relief by displaying, on display 48, the percent of treatment sessions that recorded pain relief, and the degree of pain relief most often obtained. Device 20 also displays other helpful treatment assessment data such as the most frequently used intensity for each channel, the total number of treatment sessions, and the average length of each session. By using this information, the clinician can determine a patient's progress and whether the device was used appropriately. All of this information is based upon the pain scale input, time, and intensity data stored by microprocessor 64 in non-volatile memory 66 for each treatment session.

The data stored by microprocessor 64 in memory 66 (such as beginning pain level, ending pain level, duration and intensity) is also available for review by a clinician via display 48. This data can be in raw form, or microprocessor 64 will provide analysis of the data. The data or analyzed information is displayed by microprocessor 64 on display 48 when PROG+ and PROG− inputs 52A and 52B are pressed simultaneously.

TENS device 20 allows real time measurement of subjective perceptions or sensations and provides invaluable data for determining the effectiveness of a pain treatment. Device 20 is easy to use and allows measurements to be made in the real world of the patient, i.e., in the home or at work. Further, device 20 forces the patient to consistently enter pain data, as the TENS treatment is only activated and deactivated upon entry of information on pain scale 56. The information output from device 20 can be used in a wide variety of applications and can provide a statistical correlation for evaluation a pain treatment or the consistency of the patient's response. Device 20 can automatically calculate statistical parameters, such as a trend of the patients's pain and a histogram of the patients's pain levels grouped daily, weekly, or monthly.

In conclusion, with the intensity control feature of the present invention, any time a patient activates the intensity control, a continuous train of pulses is output to assist in intensity setting. This applies even if the treatment mode happens to be in an "off time" when the patient chooses to alter the intensity setting. With the present invention, the rate and pulse width of the continuous train used during the intensity control period can be the same as the treatment mode parameters of the particular treatment mode which was then in operation. Alternatively, microprocessor 64 can use preset values of rate and pulse width for the continuous train.

The present invention adds safety and comfort to the patient using the device. The patient turning the intensity control up during an off time in a periodic treatment mode will not surprised by a high intensity stimulation at the start of on time. Similarly, an unpleasant surprise will not occur if the periodic treatment mode happened to be in a reduced stimulation time of a modulation mode when intensity adjustment is made.

With the present invention, a separate continuous mode need not be selectable by the patient. A patient selectable continuous mode can be eliminated since it is primarily used for intensity control. This reduces the risk of over stimulation as a result of the patient selecting a continuous treatment mode, when a periodic treatment mode is more appropriate.

With the present invention, the patient is assisted in his or her desire to modify intensity. An intensity adjustment can be made at any time during treatment without the risk of any unpleasant surprises. The patient will not be frustrated by inactive intensity adjustment control (as the case in some prior art devices) and will not be surprised by an unexpected onset of full stimulation caused by changing intensity settings during an off time of a periodic treatment mode.

Although the present invention has been described with reference to preferred embodiments, workers skilled in the art will recognize that changes may be made in form and detail without departing from the scope of the invention.

What is claimed is:

1. In a medical stimulator having a plurality of treatment modes for supplying trains of electrical pulses through electrodes to a patient, and including a pulse generator for electrical pulses and an intensity control for adjusting intensity of stimulation pulse trains supplied through electrodes to the patient, the improvement comprising:

a control responsive to actuation of the intensity control for causing the pulse generator to generate a continuous train of pulses while the intensity control is actuated by the patient.

2. The invention of claim 1 wherein the control includes means responsive to the intensity control for returning operation of the stimulator to a previous treatment mode which preceded actuation of the intensity control when the intensity control has been inactive for a predetermined time following actuation of the intensity control.

3. A medical stimulator which provides a periodic electrical stimulation signal through electrodes to a patient, the stimulator comprising:

a pulse generator for generating electrical pulses which form the stimulation signal;

a stimulation signal mode control for switching the stimulation signal between an on time cycle where in the stimulator supplies a continuous train of electrical pulses to the patient and an off time cycle wherein no stimulation is supplied to the patient;

an intensity control for adjusting intensity of stimulation pulse trains supplied to the patient during the on time cycle; and a switching control responsive to actuation of the intensity control for causing the stimulator to generate the continuous train of pulses while the intensity control is actuated.

4. The medical stimulator of claim 3 and further comprising:

a first and a second channel coupled to the pulse generator for transmitting the stimulation signal;

a first and a second electrode connected to the stimulator via the first channel for providing the stimulation signal to the patient; and a third and a fourth electrode connected to the stimulator via the second channel for providing the stimulation signal to the patient.

5. The medical stimulator of claim 4 wherein the intensity control comprises:

a first channel intensity control for adjusting intensity of stimulation pulse trains supplied to the patient via the first channel; and a second channel intensity control for adjusting intensity of stimulation pulse trains supplied to the patient via the second channel.

6. A medical stimulator operable in a plurality of user selectable modes of operation, the stimulator comprising:

mode selection means for selecting a first mode of operation;

a stimulation signal generator coupled to the mode selection means for generating a stimulation signal based on the selected mode of operation;

an electrode coupled to the stimulation signal generator for applying the stimulation signal to a patient;

intensity adjustment means coupled to the stimulation signal generator for adjusting the intensity of the stimulation signal; and means for overriding the selected mode of operation while the intensity adjustment means is being operated and providing a substantially continuous stimulation signal during operation of the intensity adjustment means.

* * * * *